United States Patent [19]
Beinecke

[11] Patent Number: 5,887,807
[45] Date of Patent: Mar. 30, 1999

[54] SYRINGE DISPOSAL SYSTEM

[75] Inventor: Gregory L. Beinecke, St. Louis, Mo.

[73] Assignee: BK Environmental Products, St. Charles, Mo.

[21] Appl. No.: 817,551

[22] PCT Filed: Oct. 5, 1995

[86] PCT No.: PCT/US95/12966

§ 371 Date: Jul. 7, 1997

§ 102(e) Date: Jul. 7, 1997

[87] PCT Pub. No.: WO96/11059

PCT Pub. Date: Apr. 18, 1996

[51] Int. Cl.$^6$ .............................. B02C 18/06; B02C 19/12
[52] U.S. Cl. ............................ 241/36; 241/100; 241/235; 241/242; 241/606
[58] Field of Search .................. 241/36, 100, 236, 241/606, 235, 242

[56] References Cited

U.S. PATENT DOCUMENTS

| | | |
|---|---|---|
| 1,280,687 | 10/1918 | Dudley . |
| 1,942,500 | 1/1934 | Spang ................................. 241/235 X |
| 3,363,847 | 1/1968 | Joa . |
| 3,469,750 | 9/1969 | Vanderbeck . |
| 3,736,824 | 6/1973 | Dunnican et al. . |
| 3,750,966 | 8/1973 | Anderson ................. 241/99 |
| 3,926,379 | 12/1975 | Dryden et al. . |
| 4,269,364 | 5/1981 | Moriconi et al. . |
| 4,275,628 | 6/1981 | Greenhouse . |
| 4,332,323 | 6/1982 | Reenstierna . |
| 4,531,437 | 7/1985 | Szablack et al. . |
| 4,565,311 | 1/1986 | Pugliese et al. . |
| 4,618,103 | 10/1986 | Wilson et al. . |
| 4,619,409 | 10/1986 | Harper et al. . |
| 4,884,756 | 12/1989 | Pearson . |
| 4,905,916 | 3/1990 | Sorwick et al. . |
| 4,971,261 | 11/1990 | Solomons . |
| 5,025,994 | 6/1991 | Maitlen . |
| 5,035,367 | 7/1991 | Nojima . |
| 5,038,929 | 8/1991 | Kubofcik . |
| 5,054,696 | 10/1991 | Mennel et al. . |
| 5,064,124 | 11/1991 | Chang . |
| 5,138,125 | 8/1992 | Salesses . |
| 5,172,808 | 12/1992 | Bruno . |
| 5,212,362 | 5/1993 | Burden et al. . |
| 5,275,342 | 1/1994 | Galanty . |
| 5,354,000 | 10/1994 | Wright et al. . |
| 5,454,523 | 10/1995 | Matsuda ................................. 241/242 |
| 5,662,281 | 9/1997 | Wollert et al. .......................... 241/100 |

*Primary Examiner*—John M. Husar
*Attorney, Agent, or Firm*—David M. Klein; Shearman & Sterling

[57] ABSTRACT

A disposal system for cutting a needle/syringe (22) into small pieces. One or more motor driven rotating cutting blades (6) are located inside of a housing for cutting the needle/syringe (2) into small pieces. The pieces are deposited in a disposal tray (10) filled with a disinfecting solution, with the parts of the needle/syringe (2) automatically separating for recycling due to the specific gravity of the pieces. A pump (16) is provided for pumping the disinfecting solution, preferably a mixture of chlorine bleach and water, to the needle/syringe inlet (8) and cutting area. The disinfecting solution continuously disinfects the inlet (8), the needle/syringe pieces, the cutting blade (6) and the disposal tray (10). An automatic timer deeps the cutting blades (6) rotating and the pump (16) operating for a sufficient time to cut the needle/syringe (2) and disinfect the apparatus. A chute assembly prevents pieces of the disintegrated blade from flying out of the inlet (8) and provides and auto on/auto off feature.

25 Claims, 8 Drawing Sheets

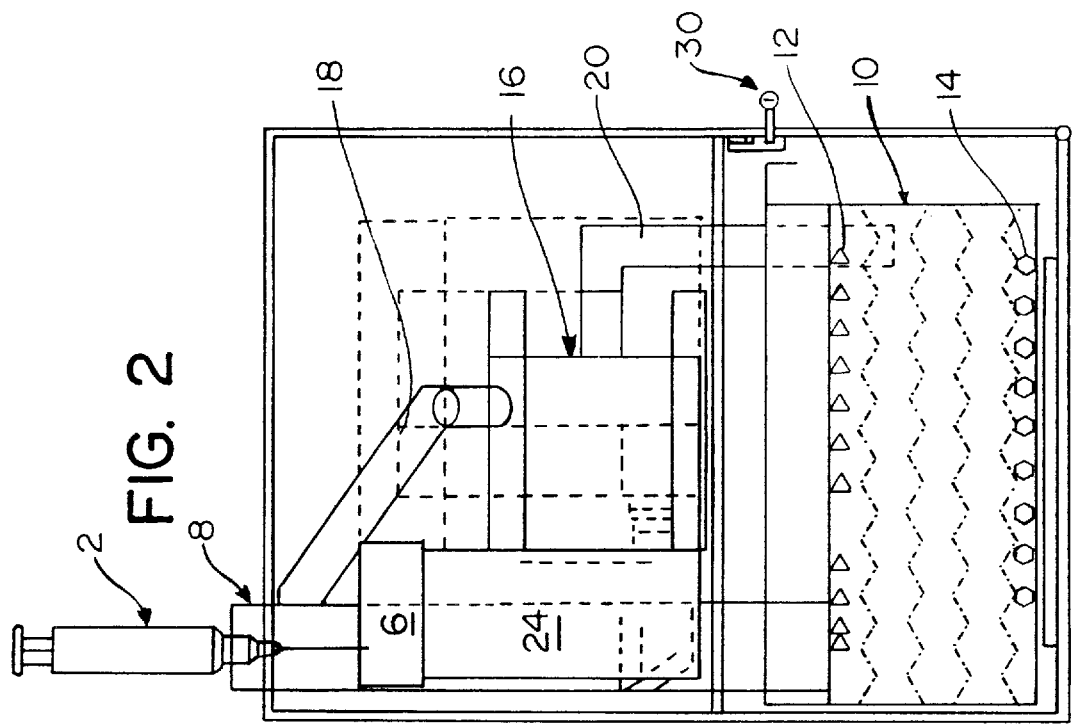
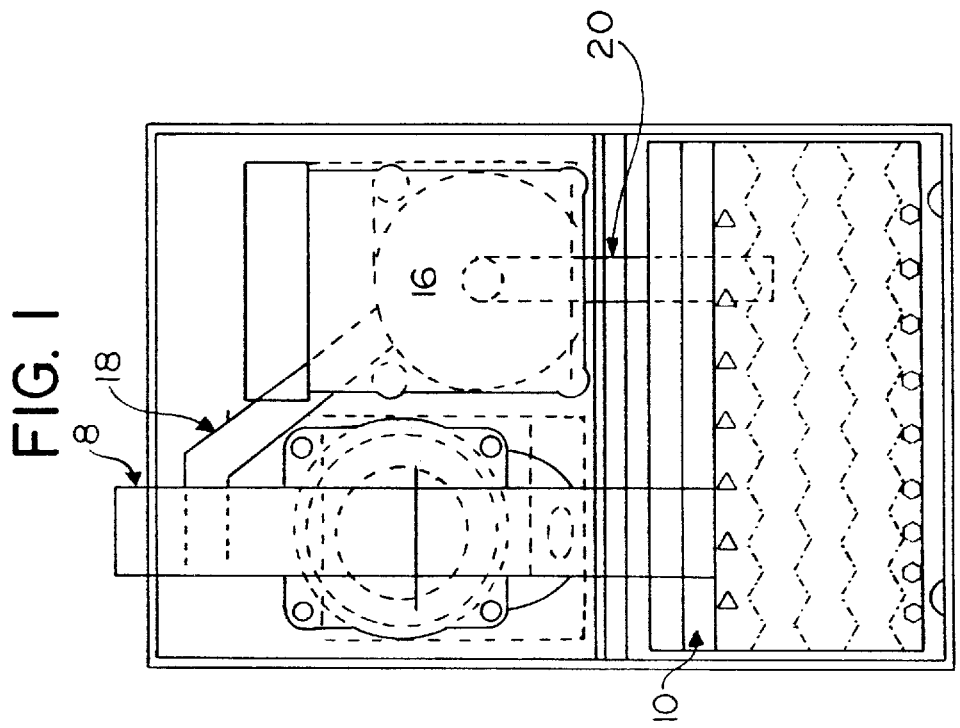

FIG. 7B
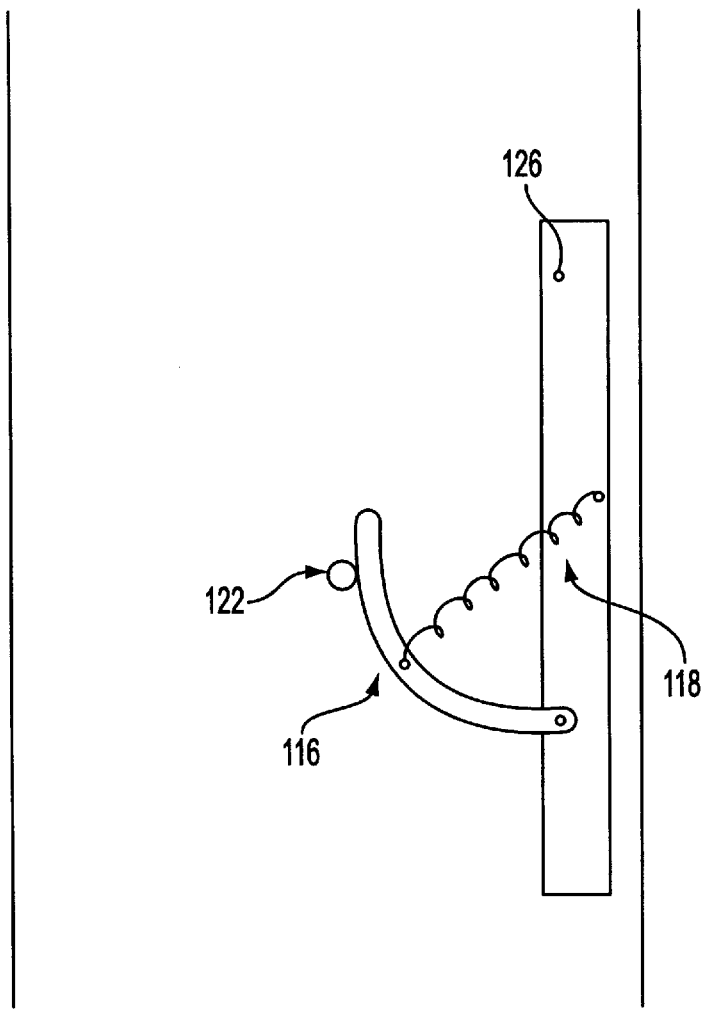
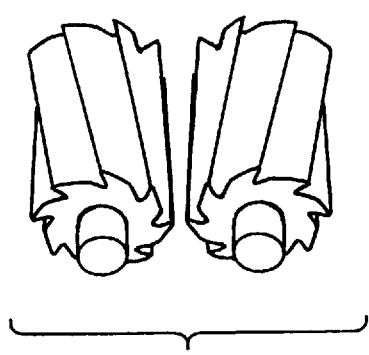
FIG. 11B

SYRINGE DISPOSAL SYSTEM

BACKGROUND OF THE INVENTION

1. Field of the Invention

The present invention relates generally to a disposal system for needles and syringes, and more particularly to a needle/syringe disposal system which incorporates a cutting device for cutting the needle/syringe into small pieces which may be separated for recycling, and a self-contained sterilization and decontamination system.

2. Description of the Related Art

Devices for destroying and disposing of used syringes are well known in the art. In one type of syringe disposal system, a container is provided for disposing of used syringes. For example, U.S. Pat. No. 5,038,929 discloses a syringe disposal system which comprises numerous elongated aligned receptacles for receiving sharp instruments. Each container contains a curable liquid in which the used syringe is inserted. The liquid then cures, sealing the syringe in the hardened material. Other examples of such containers are shown, for example, in U.S. Pat. Nos. 1,280,687 and 5,172,808.

In another type of syringe disposal device, an apparatus is provided for breaking off or rendering useless the needle of the syringe. U.S. Pat. No. 3,469,750 discloses an apparatus which incorporates a pair of coaxially movable shearing blades. A syringe is inserted in the device, and the blades moved relative to each other for shearing the needle from the cannula, and the cannula from the syringe body. Another such device is shown in U.S. Pat. No. 4,275,628 which includes lever driven blades which sever the needle and cannula from the syringe.

U.S. Pat. No. 3,736,824 discloses an elongated receptacle for receiving the cannula and needle of a syringe. A lever is provided for severing the needle, which falls into a receptacle. U.S. Pat. No. 4,332,323 discloses a device for bending the needle of a syringe thereby rendering it useless. U.S. Pat. No. 5,212,362 discloses a further apparatus for rendering useless the needle of a syringe. This device includes electrical means for killing infectious agents which may be present on the needle.

In order to improve upon the manually operated devices for destroying syringes, U.S. Pat. No. 4,565,311 discloses an electrically driven apparatus for destroying used syringes. A pair of blades is provided which are moved by a motor driven linear actuator to cut the syringe into three pieces.

Other motor driven disposal devices are shown, for example, in U.S. Pat. Nos. 3,926,379; 5,054,696; 4,619,409; and 4,269,364.

Each of these devices include shortcomings that are overcome by the needle/syringe disposal system of the present invention.

SUMMARY OF THE INVENTION

The present invention is a needle/syringe disposal system for cutting a needle/syringe into small pieces (preferably 1–2 mm or less) for disposal or recycling. The system is contained in an enclosed hollow housing which has an inlet for inserting a needle/syringe to be destroyed. The inlet extends between the exterior of the housing and one or more rotating cutting blades inside the housing. The cutting blades are rotated by a motor and are adapted for cutting a needle/syringe inserted through the inlet into small pieces by continuous rotation of the cutting blade.

A disposal tray is located below the rotating cutting blade(s) for receiving the ground up needle/syringe pieces. The system preferably includes one or more rotating blades which cut the needle/syringe into small pieces.

A pump is provided for pumping a disinfecting solution, preferably a mixture of chlorine bleach and water, from a disinfecting solution supply to the inlet area. The disinfecting solution is sprayed into the inlet and flows through the cutting area. Thus, the inlet, the needle/syringe pieces, the cutting blade and the disposal tray are continuously disinfected. In a preferred embodiment, the disinfecting solution is pumped from the disposal tray. In this embodiment, the solution serves the added function of separating the parts of the needle/syringe in the disposal tray, since the plastic pieces of the syringe will float, and the metal parts of the needle will sink in the solution. The housing of the system may be opened to enable the disposal tray to be removed from the housing.

An automatic timer may be used to keep the cutting blade rotating for a sufficient amount of time to fully grind the needle/syringe. A timer may also be used to keep the pump operating for a predetermined amount of time after the needle/syringe has been ground.

A portable embodiment of the invention is battery driven. A safety chute assembly includes an inner chute movable within an outer chute. A trap door on the inner chute is opened as the chute is lifted to enable the syringe to fall into contact with the moving blade. The trap door then closes and the inner chute and trap door may be used as a pusher to push the syringe into the blade.

BRIEF DESCRIPTION OF THE DRAWINGS

FIG. 1. is a schematic front view of the needle/syringe disposal system of the present invention.

FIG. 2 is a schematic side view of the needle/syringe disposal system of the present invention.

FIG. 7B is a partial exploded side view of a further alternative chute mechanism.

DESCRIPTION OF THE PREFERRED EMBODIMENT

Figure 3:
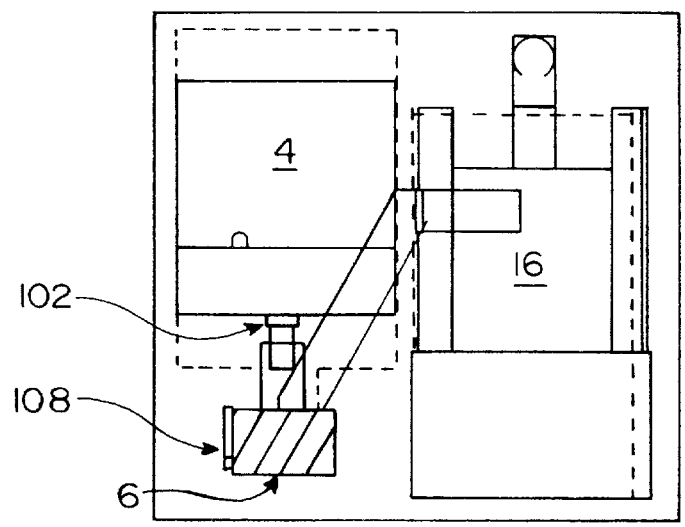
FIG. 3 is a schematic top view of the needle/syringe disposal system of the present invention.

As shown in FIGS. 1–12, the present invention is a self-contained device for cutting needles, syringes and the like into small pieces which may be easily separated for recycling, and for sterilizing the otherwise contaminated pieces of the needle/syringe. While the device will be described with respect to disposal of a syringe, it is understood that syringe will be understood to refer to syringes, needles, and combinations thereof.

The system includes a motor 4 which drives one or more cutting blades 6. An inlet 8, preferably located in the top of the disposal device, is aligned with the cutting blades 6 so that a syringe 2 may be inserted through the top of the device and ground by cutting blades 6. Depending upon the types of cutting blades 6 in use, the syringe may be drawn into the cutting blades by the force of gravity, or may be pulled into the device by the rotating action of the blades 6.

Motor 4 is a conventional electrically driven motor which may be powered by batteries 100, preferably a conventional 14.4 Volt battery pack, in a portable unit (FIG. 12), or plugged into a conventional wall outlet (not shown) in a non-portable embodiment (FIGS. 1–6). If desired, a transformer may be provided which would enable the device to be operated in either a permanent plugged-in mode or a portable mode. Electrical connections to the motor 4 may be by any means conventionally known in the art. Motor 4 may be air driven if a source of air is provided.

Motor 4 preferably directly drives the cutting blade 6 by means of a shaft 102 (FIG. 3). In an alternative embodiment, indirect drive means, such as a gear or gears 104 (FIG. 12) or a belt, chain pulley, or other drive means may be used to drive the blades 6. In a preferred embodiment of the invention, using the preferred blade, blade 6 is made to spin at approximately 1500–2000 rpm, and more preferably 1800–2000 rpm. The function of gear drive means 104 is to increase or decrease the blade speed to the desired speed.

Below the cutting blades 6, an outlet 24 directs the ground pieces of the syringe to a recovery tray 10 toward the bottom of the disposal device. The recovery tray 10 preferably has in it a disinfecting liquid, discussed in detail below, which kills all harmful agents on the ground syringe parts.

Figure 9:
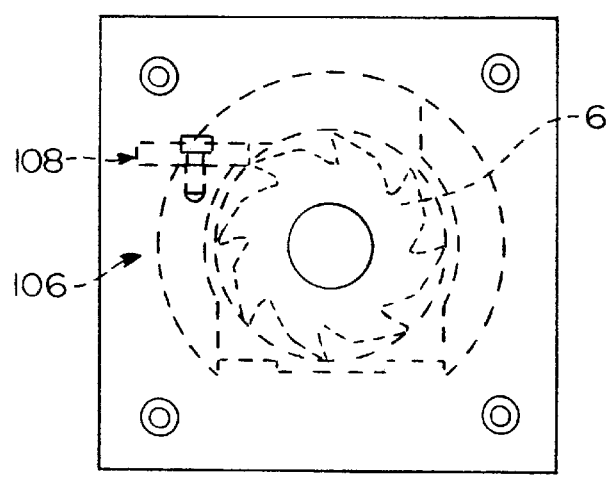
FIG. 9 is a side view of the blade housing of the present invention.
Figure 10:
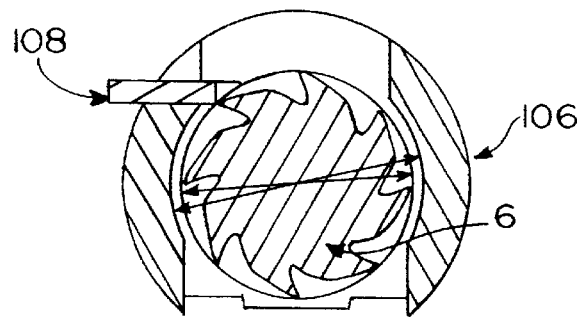
FIG. 10 is a cross-sectional side view of the blade housing of the present invention through section A—A.
Figure 11:
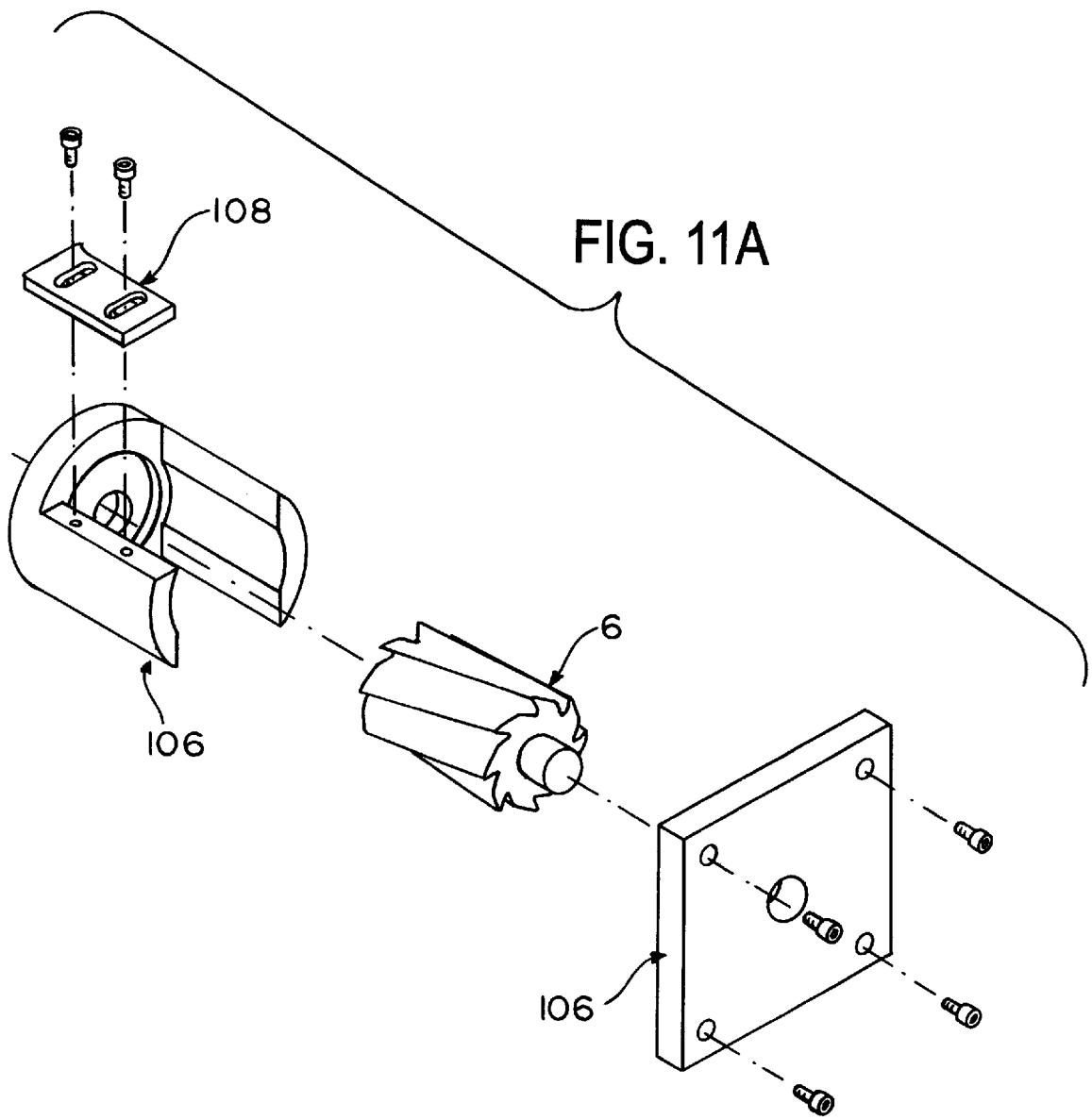
FIGS. 11A and 11B are perspective views of a single-blade embodiment of the present invention and a dual-blade embodiment of the invention respectively.

Cutting blade 6 may be any type of rotating blade known in the art which would slice, grind, or chop the syringe body and needle into relatively small pieces, on the order of 1–2 millimeters. Preferably, the depth and number of the teeth, and the speed at which the blade is rotated are established so that the blade cuts the syringe into pieces of 1–2 mm, and so that the motor is able to maintain blade speed and not bind. With too many teeth, the blade will not be able to catch the syringe to cut it. With too few teeth, the blade tends to bind. The teeth are angled at an acute angle θ with respect to the fixed cutter (described below) so that the teeth provide a continuous cutting action, like a scissor, rather than chopping the syringe as in the prior art, e.g., U.S. Pat. No. 4,269,364. The angle θ is preferably in the range of 15–75 degrees, and more preferably in the range 15–45 degrees. In a preferred embodiment, as shown in FIGS. 9–11, blade 6 preferably includes 16 teeth, each at a 30 degree flute angle, and is constructed of M2 high speed steel. Each blade tooth is on the order of 0.15" deep, and the total blade diameter is preferably about 1.75". It is foreseen that the teeth may be straight, i.e., parallel with a longitudinal axis of the blade, and the fixed cutter angled with respect to the blade to provide the same continuous cutting action.

Blades 6 may also be, for example, a helical or worm gear, which continuously cuts the syringe body. As shown in FIGS. 7–10, blade 6 is preferably contained in a blade housing 106 that is constructed of aluminum or other appropriate material. The corners of the inlet housing are preferably rounded to keep syringes from becoming jammed in the corners and from jamming the blade. A cutter 108 is preferably attached to the blade housing 106 by means of screws or other attachment means. The syringe is preferably cut between the rotating blade teeth and cutter 108. Cutter 108 may be adjusted if desired by loosening the attachment screws and moving the cutter. The edge of cutter 108 adjacent to the blade may be sharpened, if desired. As previously discussed, the cutter may be angled with respect to the blade teeth to provide, alone or in conjunction with angled blade teeth, the aforementioned continuous cutting action.

Figure 6:
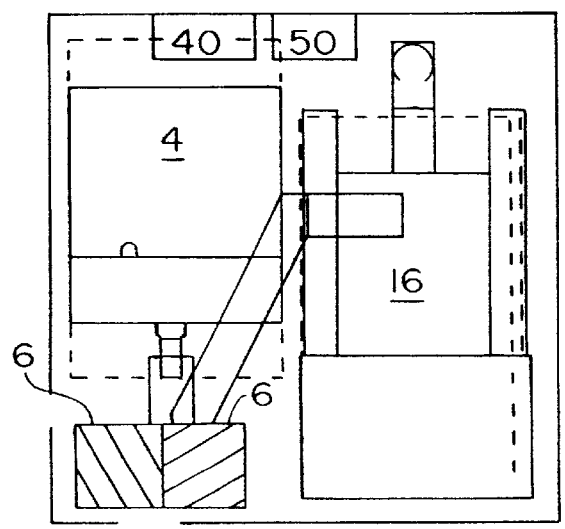
FIG. 6 is a schematic top view of an alternative embodiment of the present invention.

Alternatively, the syringe may be cut between the rotating teeth and a wall of the inlet 8. If more than one blade is used, the blades could cooperate for cutting the syringe between them (FIGS. 6 and 11B). In this embodiment, the blades would rotate in opposite directions and would draw the syringe into the inlet 8 by the downward directional movement of the gears where they meet. If two or more blades are in use, a conventionally known gear box for synchronizing the blades may be used to connect the blades to the motor 4.

Recovery tray 10 is preferably filled with a disinfectant solution in the non-portable embodiment of the invention (FIGS. 1–3). Due to the specific gravity of the materials which comprise a typical syringe, after the ground syringe pieces fall into the disinfecting solution, the plastic fragments of the syringe will float to the top of the liquid in the recovery tray 10, and the metal fragments of the syringe needle will fall to the bottom of the recovery tray 10. This enables the plastic and metal parts, which are disinfected by the disinfectant solution, to be separated for recycling.

A pump 16 is provided for circulating a disinfectant solution throughout the disposal device. In a preferred embodiment, the pump 16 includes an intake 20 which draws the disinfecting solution from the recovery tray 10. The disinfecting solution is pumped through an outlet tube 18 into the inlet area 8. A nozzle may be provided for spraying the solution into the inlet area. In this manner, the syringe is immediately treated with a disinfecting solution as it is inserted into the inlet. Also, the inlet 8, the cutting blade 6, and the outlet tube 24 are continuously disinfected by the flow of disinfecting solution.

If desired, the intake 20 to pump 16 may be inserted into a separate disinfecting solution supply, i.e., a bottle or tray full of fresh disinfecting solution. The recovery tray 10 may then be inserted into the system either empty or partially empty and as the fresh disinfecting fluid is drawn through the pump and passed through the inlet and cutting areas, it will fill the recovery tray.

The disinfecting solution may be any type conventionally known in the art, and may vary depending upon the types of infectious agents which are to be killed. In a preferred embodiment, the disinfecting solution is a mixture of chlorine bleach and water. Preferably, the disinfecting solution includes a concentration of free chlorine per liter of water of 50–10,000 parts per million.

Once a syringe has been ground, it is preferred to keep the disinfecting solution flowing through the inlet and cutting area for at least 10 minutes in order to kill any remaining infectious agents in these areas. Thus, a timer may be provided which is either automatically activated when a syringe 2 is inserted through the inlet 8, or may be manually activated by a conventionally known switch. The timer keeps the pump 16 running for a predetermined amount of time after the syringe has been ground and assures that the unit is properly disinfected. A timer may also be provided for motor 4 which is automatically activated when a syringe is placed through the inlet 8 or which may be manually activated. In the automatic embodiment, when the syringe 2 is inserted through the inlet 8, the motor 4 and the pump 16 will each be activated. A predetermined time after the switch has been activated, say one minute, the motor 4 will turn off and the pump 16 will continue to operate for a further predetermined amount of time, preferably ten minutes or more. The timing circuit may be any suitable timing circuit known to those skilled in the art. In an alternative embodiment shown in FIG. 5, the inlet 8 may be covered by a hinged door 40. The opening of hinged door 40 could initiate the timing circuit using a conventional switch.

In an alternative embodiment, (FIGS. 7 and 12), the syringe is inserted into a hollow inner inlet chute or feed tube 110 which includes one or more handles 112 located at the top of the inner inlet chute. Inner inlet chute is open at each end, and is covered at the end nearest the blade by a trap door 114 which is rotatably connected to the inner chute so that the door may open and close as described below. A cam arm 116 is attached to the trap door so that as the arm is rotated upward, the door will close, and as the arm is rotated downward, the door will open. The cam arm 116 is biased upward by a spring 118, so that the door will return to the closed position in the absence of outside forces on the cam arm 116.

The inner chute 110 is movable within an outer chute 120 that is sized to enable the inner chute to be insertable therein and removable therefrom with little play. Outer chute 120 is also generally rectangular and open at each end. A trap door cam 122 is provided on the outer chute, positioned above the cam arm 116. Trap door cam is a protuberance, peg, or other raised portion suitable for biasing cam arm 116 as the inner chute is lifted. As the inner chute 110 is lifted, cam arm 116 will contact with trap door cam 122, thereby applying a downward force on cam arm 116 and causing the trap door to open. Once the trap door opens, the syringe falls into contact with the rotating blade, and is disintegrated. It is necessary to lift the inner chute sufficiently so that the cam arm no longer contacts the cam, which will result in the closing of the trap door under the bias of the spring. The trap door and inner chute may then be used as a pusher to push the syringe into the blade as the inner chute is pushed downward. Once the trap door closes, pieces of the syringe cannot be thrown out of the inlet.

An automatic on/off switch 124 is provided at the top of the outer chute. When the inner chute is pushed all the way into the outer chute, the handle 112 will press down on the on/off switch, moving the switch to an off position. When a syringe is to be disintegrated, the inner chute is lifted, thereby turning on the motor so that the blade will be spinning at full speed when the syringe comes into contact with it so as to prevent the blade from binding. The chute is lifted past the cam, at which point the trap door opens, and past the top of the cam, at which the trap door closes. The inner chute is then pushed down until the on/off switch is turned off.

Figure 7A:
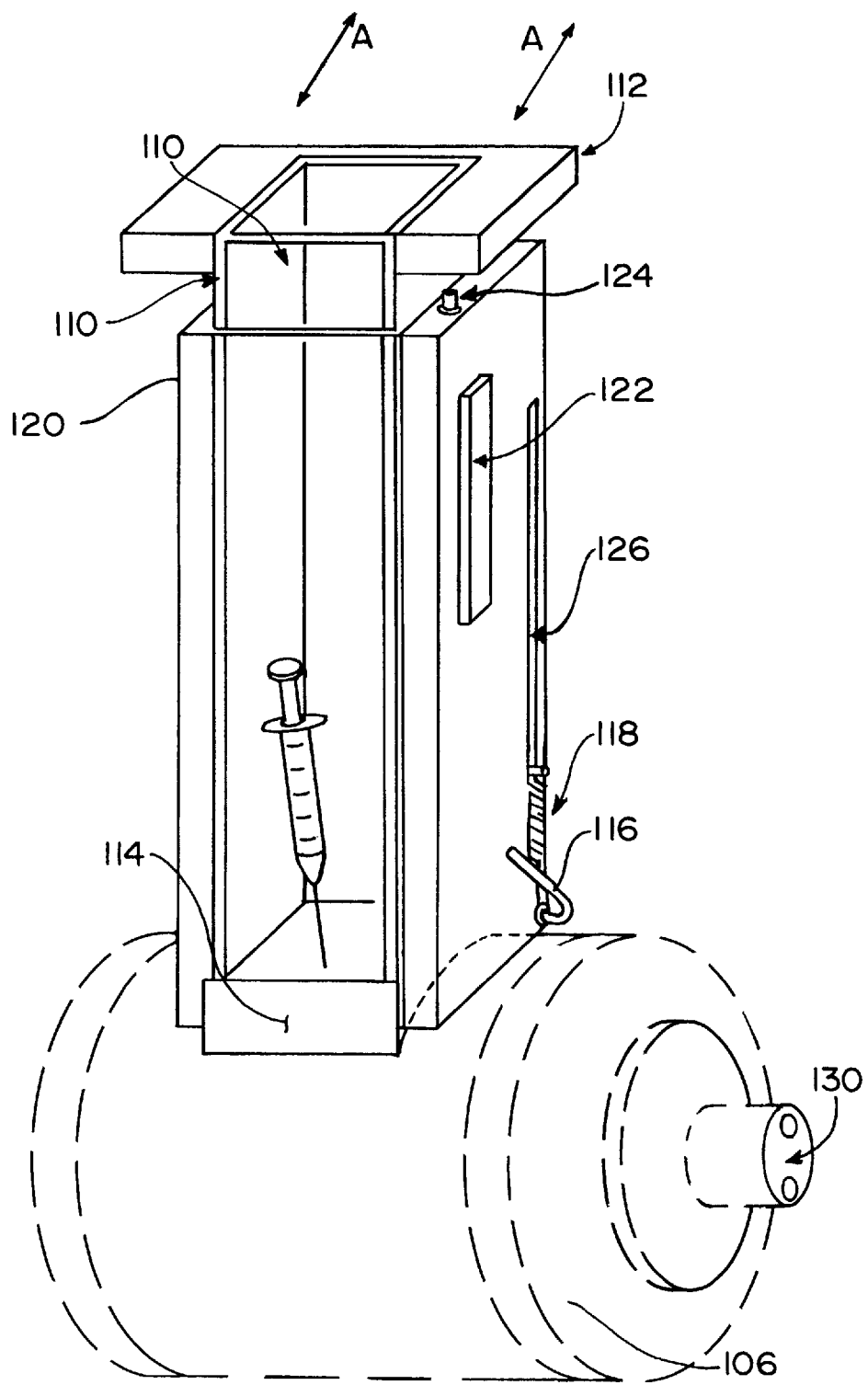
FIG. 7A is a perspective view of an alternative inlet chute mechanism of the invention.
Figure 8:
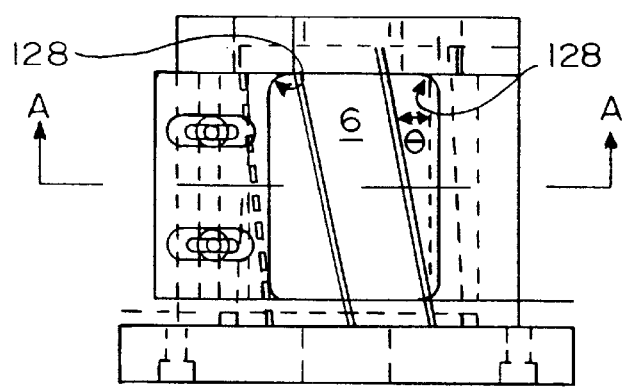
FIG. 8 is a top view of the blade housing of the present invention.

The cam 122, the cam arm 116, and the spring may be located on the inner side of the outer chute (not shown) or on the outer side of the outer chute (FIG. 7). In the latter embodiment, a slot 126 permits the cam arm and spring to pass therethrough the outer chute and allows upwards and downwards movement of the inner chute. As shown in FIG. 7B, cam arm 16 is preferably constructed of a resilient material so that as the inner chute is pushed down in the outer chute once the trap door has closed, the cam arm will bend slightly so as to clear the cam 122. Trap door cam 122 is preferably position so that the syringe will fall entirely out of the inner chute as the trap door is opened. Moreover, trap door cam 122 need only be a peg or the like provided that it has sufficient strength to bias cam arm 116.

As shown in FIG. 7, if desired, assuming that shaft 130 and motor (not shown) are supported by means of a bearing assembly, or other support is provided as will be appreciated by those skilled in the art, the entire feed chute assembly, including the inner and outer chutes 110, 120 and the blade housing 106 may be rotated back and forth in the direction A. This feature enables the device to be used by multiple personnel that dispose of many syringes and that work in close proximity to one another, for example in blood banks. Each user could rotate the feed tube toward them prior to using the device.

Figure 4:
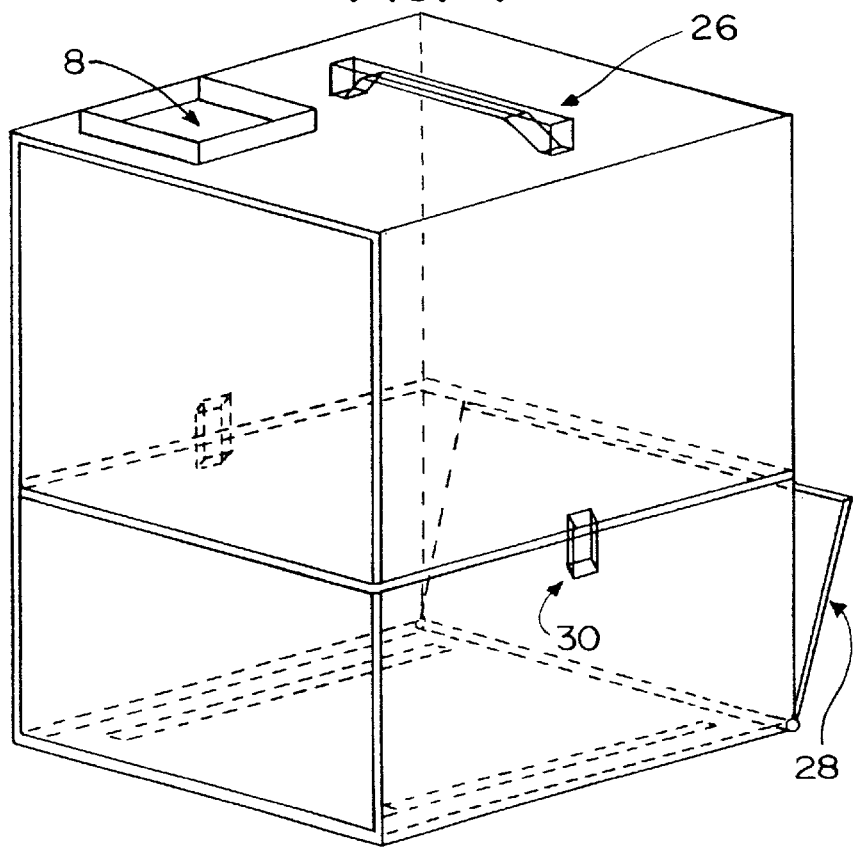
FIG. 4 is a perspective view of the exterior of the needle/syringe disposal system of the present invention.
Figure 5:
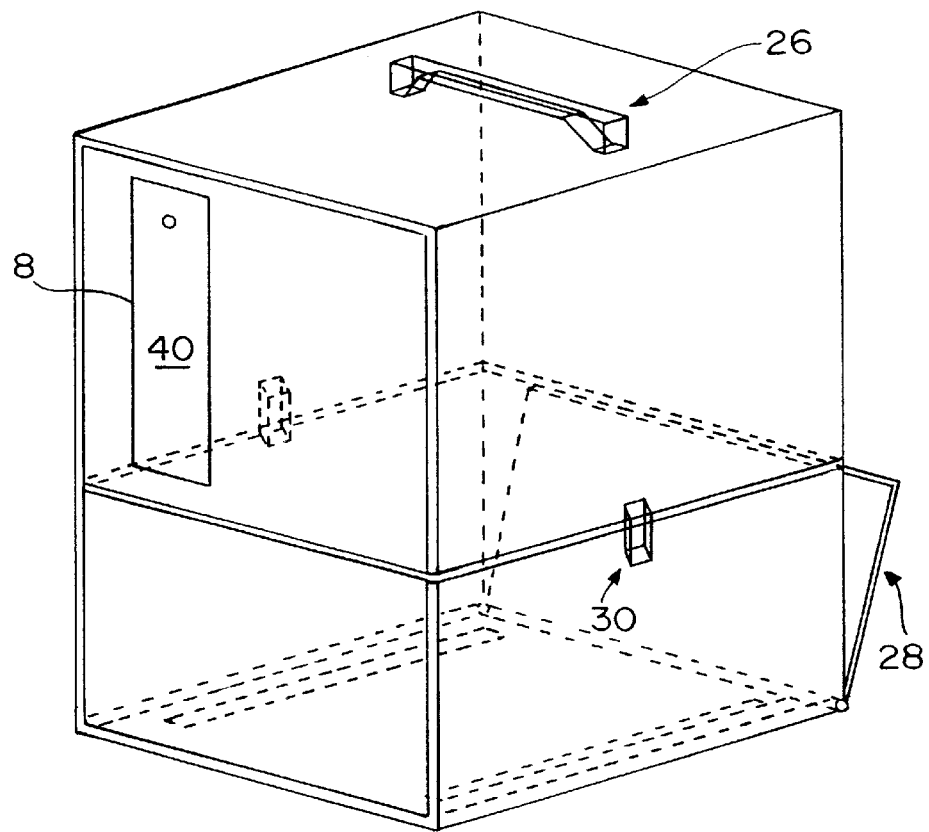
FIG. 5 is a perspective view of the exterior of the needle/syringe disposal system of the present invention which utilizes an alternative type of inlet.

The device is preferably constructed of plastic and metal materials, or any other non-corrosive materials suitable for the present application. As shown in FIG. 4, if desired, the present syringe disposal system may be housed in a self-contained portable unit having a carrying handle 26. In order to insert and remove disposal tray 10 or the optional disinfecting solution storage bottles, the lower portion of the housing 28 is hinged for exposing the interior of the device. A latch 30 allows the housing door 28 to be opened and locked.

Figure 12:
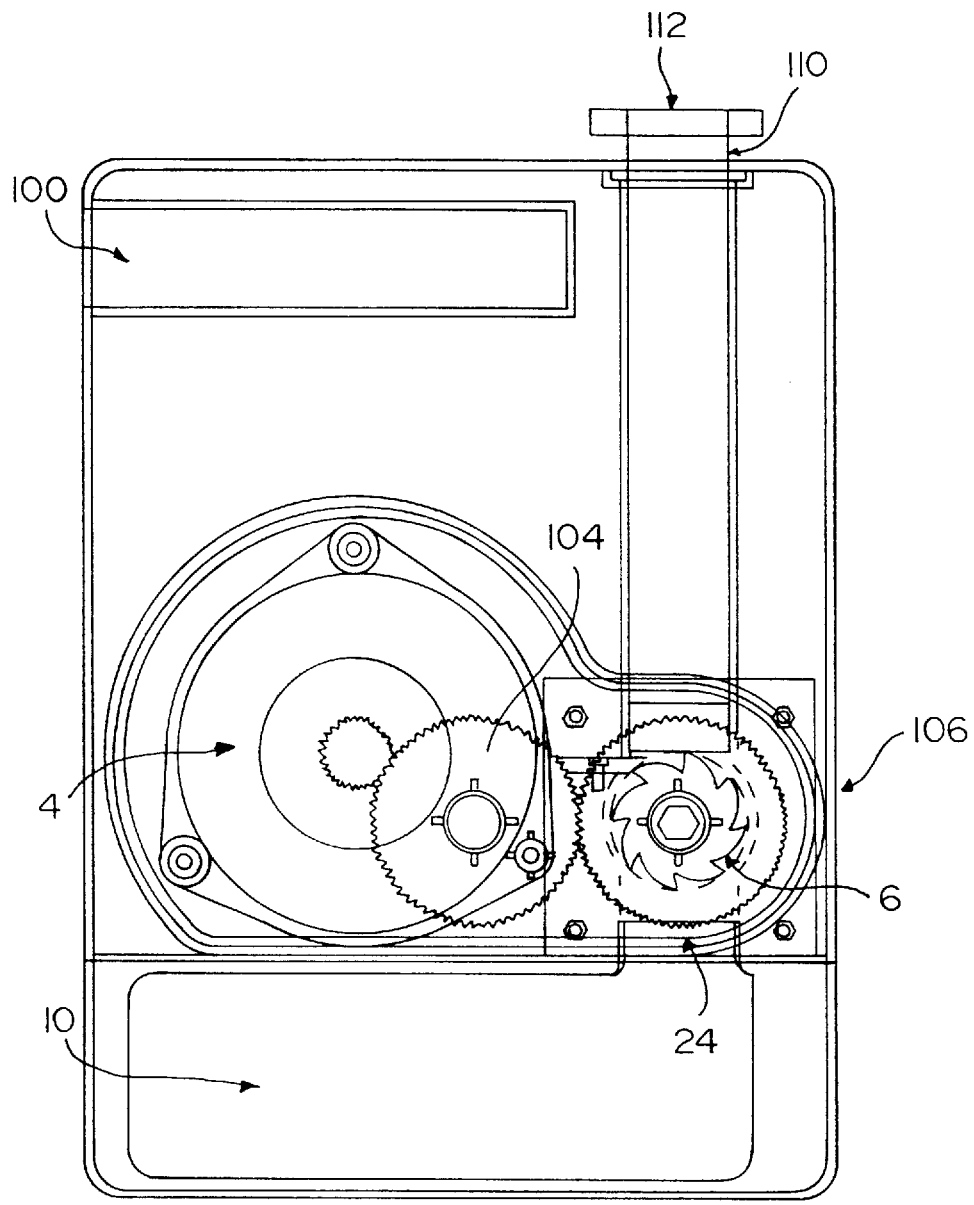
FIG. 12 is a cross-sectional side view of an alternative embodiment of the invention in which the device is portable.

In a highly portable unit, FIG. 12, the device does not use a disinfection system, and may be attached to the belt of a user, or carried around the neck.

In order to reduce the tendency of the disinfecting solution or the ground syringe parts from being ejected or splashed out through the inlet 8, the interior of the syringe disposal system may be vacuum pressurized. A vacuum pump located inside the housing would pump air from the interior of the housing to the exterior of the housing through a vent. This would cause the pressure inside the housing to be lowered causing air to be drawn in through inlet 8.

Although the present invention has been described in detail with respect to certain embodiments and examples, variations and modifications exist which are within the scope of the invention as defined in the following claims.

What is claimed is:

1. A syringe disposal system for cutting a syringe into pieces for disposal or recycling, the system comprising:
   an inlet chute having an entry end and an exit end, the inlet chute sized to receive a syringe therethrough;
   a cylindrical cutting blade comprising a plurality of parallel cutting edges on the exterior surface thereof, the cutting blade positioned aligned with the exit end of the inlet chute with a central axis of the inlet perpendicular to the longitudinal axis of the cutting blade;
   means for rotating the cutting blade;
   a cutter closely aligned with the parallel cutting edges, the parallel cutting edges of the blades aligned at an acute angle relative to the cutter, the cutter cooperating with the parallel cutting edges for cutting a syringe inserted through the inlet into pieces, at least one cutting edge of the cutting blade cooperating with the cutter at any given time for providing continuous cutting during rotation of the cutting blade; and
   a disposal tray aligned with the rotating cutting blade for receiving the pieces of the cut syringe.

2. The syringe disposal system according to claim 1 wherein the means for rotating the cutting blade is an electrically driven motor.

3. The syringe disposal system according to claim 1 wherein the cylindrical cutting blade is a first cutting blade, and further comprising a second rotating cutting blade, the first and second cutting blades cooperating with each other for cutting the syringe into pieces.

4. The syringe disposal system according to claim 1 which comprises an outlet tube aligned with the cutting blade, the outlet tube directing the cut pieces of the syringe from the blade to the disposal tray.

5. The syringe disposal system according to claim 1 further comprising:

a source of disinfecting solution; and a pump for pumping disinfecting solution from the source of disinfecting solution to the inlet chute, the disinfecting solution disinfecting the inlet chute, the syringe pieces, and the cutting blade and accumulating in the disposal tray.

6. The syringe disposal system according to claim 5 wherein the source of disinfecting solution is contained within the disposal tray.

7. The syringe disposal system according to claim 5 wherein the cylindrical cutting blade is a first cutting blade, and further comprising a second rotating cutting blade, the first and second cutting blades cooperating with each other for cutting the syringe into pieces.

8. The syringe disposal system according to claim 9 which comprises an outlet tube aligned with the cutting blade, the outlet tube directing the cut pieces of the syringe from the blade to the disposal tray, the disinfecting solution disinfecting the outlet tube.

9. The syringe disposal system according to claim 5 wherein the disinfecting solution comprises a mixture of chlorine bleach and water.

10. The syringe disposal system according to claim 5 further comprising a vacuum pump in the housing for de-pressurizing the inlet chute.

11. The syringe disposal system according to claim 5 further comprising a timer which is activated manually or when a syringe is inserted into the inlet chute, the timer causing the pump to operate for a predetermined amount of time.

12. The syringe disposal system of claim 1 wherein the disposal tray comprises disinfecting solution.

13. The syringe disposal system according to claim 1 further comprising a housing containing the inlet chute, the cutting blade, the cutter, the means for rotating the cutting blade, and the disposal tray, the housing being openable for enabling the disposal tray to be removed from the housing.

14. The syringe disposal system according to claim 1 further comprising a vacuum pump in the housing for de-pressurizing the inlet chute.

15. The syringe disposal system according to claim 1 further comprising an automatic timer that is activated when a syringe is inserted into the inlet chute, the timer causing the means for rotating the cutting blade to operate for a predetermined amount of time.

16. The syringe disposal system according to claim 1 wherein the cutter is a fixed blade oriented parallel to the longitudinal axis of the cutting blade and wherein the parallel cutting edges of the blade are at an acute angle relative to a longitudinal axis of the blade.

17. The syringe disposal system according to claim 1 wherein the cutter is a fixed blade oriented at an acute angle relative to a longitudinal axis of the cutting blade and wherein the parallel cutting edges of the blade are parallel to the longitudinal axis of the blade.

18. The syringe disposal system according to claim 1 wherein the inlet chute comprises:

a hollow outer chute and a hollow inner chute, each having an entry end and an exit end, the inner chute being slidable within the outer chute;

a door for opening and closing the exit end of the inner chute; and means for automatically opening the door while raising the inner chute for enabling a syringe to fall through the exit end of the inner chute, and for closing the door while lowering the inner chute once the syringe passed through the exit end of the inner chute.

19. The syringe disposal system according to claim 1 further comprising automatic on/off switch means for turning the means for rotating the cutting blade on once the inner chute is lifted and for turning the means for rotating the cutting blade off once the inner chute has been lowered.

20. An inlet chute for a syringe disposal system which comprises:

a hollow outer chute having an entry end and an exit end;

a hollow inner chute having an entry end and an exit end, the inner chute being slidable within the outer chute;

a door for opening and closing the exit end of the inner chute; and means for automatically opening the door while raising the inner chute for enabling a syringe to fall through the exit end of the inner chute, and for closing the door once the syringe passed through the exit end of the inner chute into a cutter.

21. The inlet chute according to claim 20 wherein the means for automatically opening the door comprises:

biasing means for biasing open the door while raising the inner chute; and return means for closing the door during downward movement of the inner chute.

22. The inlet chute according to claim 21 wherein the biasing means comprises a cam on the outer chute that interacts with an arm on the door, and the return means comprises a spring attaching the door to the inner chute.

23. The inlet chute according to claim 20 wherein the means for automatically opening the door comprises:

biasing means for biasing open the door while raising the inner chute; and return means for closing the door during further upward movement of the inner chute.

24. The inlet chute according to claim 23 wherein the biasing means comprises a cam on the outer chute that interacts with an arm on the door during upward movement of the inner chute, and the return means comprises a spring attaching the door to the inner chute, the arm passing the cam during the further upward movement and the return means then closing the door during such further upward movement.

25. The inlet chute according to claim 24 wherein the arm is constructed of a resilient material.

* * * * *